(12) United States Patent
Eiermann et al.

(10) Patent No.: US 6,407,230 B1
(45) Date of Patent: Jun. 18, 2002

(54) METHOD FOR PRODUCING LACTAMS USING OLIGOPHOSPHATE CATALYSTS

(75) Inventors: Matthias Eiermann, Limburgerhof; Andreas Ansmann, Wiesloch; Klemens Flick, Herxheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/646,153

(22) PCT Filed: Mar. 8, 1999

(86) PCT No.: PCT/EP99/01463

§ 371 (c)(1),
(2), (4) Date: Sep. 14, 2000

(87) PCT Pub. No.: WO99/47500

PCT Pub. Date: Sep. 23, 1999

(30) Foreign Application Priority Data

Mar. 18, 1998 (DE) .......................................... 198 11 880

(51) Int. Cl.[7] ............................................. C07D 201/08
(52) U.S. Cl. ....................................................... 540/539
(58) Field of Search ......................................... 540/539

(56) References Cited

U.S. PATENT DOCUMENTS

| 2,357,484 A | 9/1944 | Martin | ........................ 260/239 |
|---|---|---|---|
| 5,493,021 A | 2/1996 | Barratt et al. | ................ 540/539 |
| 5,646,277 A | 7/1997 | Fuchs et al. | ................. 540/539 |

FOREIGN PATENT DOCUMENTS

| DE | 43 19 134 | 12/1994 |
|---|---|---|
| DE | 43 39 648 | 5/1995 |
| EP | 659 741 | 6/1995 |
| WO | WO 95/14665 | 6/1995 |
| WO | WO 96/16936 | 6/1996 |
| WO | WO 96/18726 | 6/1996 |
| WO | WO 96/22974 | 8/1996 |
| WO | WO 99/28296 | 6/1999 |

Primary Examiner—Bruck Kifle
(74) Attorney, Agent, or Firm—Keil & Weinkauf

(57) ABSTRACT

A process for preparing lactams by hydrolytic cyclization of aminonitriles in the gas phase in the presence of a metal phosphate catalyst comprises using a catalyst comprising one or more oligophosphates of the general formula (I)

$$M(PO_a)_b \qquad (I)$$

where M is a metal of group 3 or 4 of the periodic table, including the lanthanides, a is >2.5 and <4.0, and b is such that electrical neutrality is ensured, or a mixture of one or more oligophosphates of the general formula (I) with one or more further salts of a metal of group 3 or 4 of the periodic table, including the lanthanides, with an inorganic acid.

7 Claims, No Drawings

METHOD FOR PRODUCING LACTAMS USING OLIGOPHOSPHATE CATALYSTS

Lactams are versatile compounds. For instance, N-methylbutyrolactam (N-methylpyrrolidone) is a widely used solvent and e-caprolactam is an important monomer for the manufacture of polyamide fibers.

Lactams can be prepared by hydrolytic cyclization of aminonitriles in the gas phase. Catalysts having-dehydrating properties, such as aluminum oxide, silica gel or borophosphoric acid, are used.

EP-A 0 659 741 describes the preparation of lactams from aminonitriles and water by hydrolytic cyclization in the gas phase using metal orthophosphates, especially aliminum, zirconium, niobium and lanthanum orthophosphates, as catalysts. The catalysts may additionally be impregnated with basic alkali or alkaline earth metal compounds, preferably of cesium rubidium and potassium.

However, the selectivity of the prior art catalysts still leaves something to be desired. The formation of by-products makes it difficult to isolate the lactams and may lead to poisoning of the catalysts used.

It is an object of the present invention to provide a catalyst for preparing lactams by hydrolytic cyclization of aminonitriles that is highly selective at high rates of conversion.

We have found that this object is achieved by a process for preparing lactams by hydrolytic cyclization of aminonitriles in the gas phase in the presence of a metal phosphate catalyst, which comprises using a catalyst comprising one or more oligophosphates of the general formula (I)

$$M(PO_a)_b \tag{I}$$

where M is a metal of group 3 or 4 of the periodic table, including the lanthanides, a is >2.5 and <4.0, and b is such that electrical neutrality is ensured, or a mixture of one or more oligophosphates of the general formula (I) with one or more further salts of a metal of group 3 or 4 of the periodic table, including the lanthanides, with an inorganic acid.

The catalyst used may comprise one or more oligophosphates of the general formula (I). Said formula (I) must be understood as gross stoichiometric formula and not as the molecular formula of actual existing compounds. Oligophosphates for the purposes of the present invention are phosphates which are formally derived from acids which are obtainable by condensation of orthophosphoric acid with elimination of water. The condensation of orthophosphoric acid $H_3PO_4$ with intermolecular elimination of water yields chain-like oligophosphoric acids $H_{n+2}P_nO_{3n+1}$ (tri-, tetra-, pentaphosphoric acid etc.; n=3, 4, 5, etc.) or (for large n) polymeric polyphosphoric acids. Triphosphoric and higher acids may also undergo an intramolecular condensation to form ring-shaped metaphosphoric acids $H_nP_nO_{3n}$ (tri-, tetrametaphosphoric acid etc.; n=3, 4, etc.), and not only a chain-extending but a chain-branching condensation with the formation of branched ultraphosphoric acids (e.g., isotetraphosphoric acid $H_6P_4O_{13}$). The formal end product of the condensation is polymeric phosphorus pentaoxide $P_2O_5$. For the oligophosphates of the general formula (I) derived from these acids, a is between the corresponding value for polymeric phosphorus pentaoxide (2.5) and that of orthophosphate (4.0). That is, 2.5 <a<4.0. a is preferably from 2.6 to 3.5, particularly preferably from 3 to 3.5. In particular, a=3.

The choice of b is such as to ensure electrical neutrality. If the phosphorus in the oligophosphates is exclusively pentavalent phosphorus, b is especially (2a−5)/z, where z is the number of charges on the M cations.

M is a metal of group 3 or 4 (=transition group III or IV, respectively) of the periodic table, including the lanthanides, i.e., Sc, Y, Ti, Zr, Hf, La, Ce, Pr, Nd, Sm, Eu, Gd, Tb, Dy, Ho, Er, Tm, Yb and Lu, preferably a lanthanide, particularly preferably La or Ce, very particularly preferably La. The oligophosphates used according to the present invention may contain one or more species of metals M, preferably they contain just a single species of metals M.

The catalyst used may be a specific oligophosphate, preferably trimetaphosphate, or a mixture of a plurality of different oligophosphates of the general formula (I).

A very particularly preferred catalyst is trimetaphosphate, especially lanthanum trimetaphosphate ($LaP_3O_9$)

The catalysts used may further be mixtures of one or more of the aforementioned oligophosphates of the general formula (I) with one or more further salts of the aforementioned metals of group 3 or 4 of the periodic table, including the lanthanides, with inorganic acids. The metals present in the oligophosphates and in the further salts may be identical or different; they are preferably identical. Preferred further salts are the orthophosphates, sulfates, carbonates, silicates, arsenites, arsenates, antimonites, antimonates and nitrates, particularly preferably the orthophosphates of the metals mentioned.

The oligophosphates of the general formula (I) may be used alone or mixed with the further salts. In general, the ratio of further salts to oligophosphates is up to 50:1, preferably up to 10:1, particularly preferably up to 5:1, very particularly preferably from 0.1:1 to 5:1, and especially from 1:1 to 5:1.

The catalyst is further particularly preferably a mixture of trimetaphosphate and orthophosphate, especially with lanthanum as metal M.

The oligophosphates of the general formula (I) and the further salts may each contain up to 5 molecules of water per unit formula.

The catalyst is generally prepared from the nitrate, nitrite, carbonate, formate, acetate, oxalate or some other salt of an organic acid, but preferably from the nitrate of metal M and ammonium phosphate as preferred precursors. These components are intimately mixed with each other in the desired molar ratio as fine powders. The chosen molar ratio of phosphorus:metal (=b) will be present in the product (the oligophosphate or the mixture of different oligophosphates) after the reaction has taken place. After mixing, the precursors are slowly heated, for example in an open crucible, at temperatures from generally 140 to 200° C., preferably from 150 to 180° C., for generally from 2 to 48 hours, preferably from 8 to 36 hours, to decompose the precursors. This is followed by gradual heating to 250–900° C., preferably 400–650° C., for 1–8 days, preferably 2–5 days, to complete the conversion into the oligophosphate. This method makes it possible to obtain any oligophosphates having a phosphorus:metal ratio=3 as mixtures, but also, in some instances, in pure form. Trimetaphosphate, for example, is thus obtainable in pure form.

The present invention further provides a process for preparing a catalyst, which comprises the steps of:
a) preparing a mixture of ammonium dihydrogen-phosphate and the nitrate of said metal M in the desired molar ratio;
b) heating this mixture in stages to decompose the precursors and form the metal oligophosphate in a solid state reaction.

Metaphosphates are further obtainable by precipitating M as dihydropyrophosphate from a solution of a salt of M with pyrophosphoric acid $H_4P_2O_7$ and calcining the resulting precipitate to form the metaphosphate.

The present invention further provides a process for preparing a catalyst, which comprises the steps of:
a) preparing a solution comprising a salt of said metal M;
b) precipitating said metal M from this solution as dihydropyrophosphate and removing the precipitate comprising the metal dihydropyrophosphate;
c) optionally washing and drying said precipitate;
d) calcining said precipitate.

The precipitating of M as dihydropyrophosphate is preferably carried out at a pH of generally 0.5–4, preferably 0.8–2. To effect precipitation, a base may be added to a solution comprising the salt of metal M and pyrophosphoric acid to establish a certain pH. Preferred bases are ammonia, alkali metal hydroxides, primary, secondary and tertiary amines, particularly preferably ammonia. It is further possible to add a solution comprising the salt of metal M to an aqueous alkaline solution of pyrophosphoric acid. Suitable salts are water-soluble salts of metal M, preferably nitrates.

The concentration of the metal salt solution is generally from 0.1–1.5 mol/l, preferably 0.8–1.1, and that of the pyrophosphoric acid is generally 0.1–5, preferably 2–4, mol/l.

The precipitating of M as pyrophosphate may be carried out in the cold or in the heat. To prepare catalysts which consist essentially of oligophosphates of the general formula (I) and do not contain significant portions of orthophosphates, it is preferred to carry out the precipitation in the cold, particularly preferably by cooling with ice. To prepare catalysts which contain orthophosphates as further salts, the precipitation is preferably carried out in the heat, in which case the temperature is generally 30–100° C., preferably 60–90° C.

The pyrophosphate-containing precipitate is separated off, optionally washed and dried and subsequently calcined. The drying generally takes place at from 60 to 180° C., preferably at from 100 to 150° C., and the calcining generally at from 300 to 900° C., preferably at from 500 to 700° C., for generally 0.5–10 h, preferably 2–4 h.

Mixtures of oligophosphates of the general formula (I) and one or more further salts may be obtained by one of the following methods:

- by solid state reaction of a nitrate of metal M, ammonium dihydrogenphbsphate and an ammonium salt of the inorganic acid from which the further salts were derived;
- by coprecipitation of dihydropyrophosphates of metal M and further salts and subsequent calcination;
- by evaporating solutions comprising phosphoric acid or oligophosphoric acids, optionally other inorganic acids and also the metal M, which originates from the corresponding oxide in the desired molar ratio, and optionally subsequent calcination.

The catalyst materials may be used in any desired form, for example as powders, as spall or as molded shapes. Examples of molded shapes for the catalyst materials are extrudates or spheres. A binder may be added to produce the molded shapes, for example Aerosil, potato starch or cellulose ether (e.g., Walocel®). The catalyst materials may further be applied to a support, such as argillaceous earth, silica gel, carbon, silicon carbide or silicon nitride.

The catalyst is preferably used in the form of spall or molded shapes. The catalyst bed may have mixed into it additional, selectivity-enhancing components, in an amount of up to 70% by volume. Examples are silicon dioxide, silicon nitrite and silicon carbide, preferably silicon dioxide, particularly preferably quartz. Useful aminonitriles for the process of the present invention are aliphatic aminonitriles having at least two, preferably from 3 to 20, atoms in the chain between the amino group and the nitrile group. In general, these atoms are carbon atoms, but it is also possible for the chain to contain one or more, but preferably not more than 3, boron, nitrogen, phosphorus, oxygen and/or sulfur atoms in nonadjacent, but otherwise discretionary position. The amino group may be monosubstituted by a straight-chain or branched alkyl group having up to 20 carbon atoms, for example by methyl, ethyl, n-propyl, isopropyl, n-butyl, sec-butyl or tert-butyl. The aminonitriles used in the process of the present invention are preferably aminonitriles having 3, 4, 5 or 6 carbon atoms in the chain between the amino and the nitrile group without hetero atoms, particularly preferably with primary amino groups, such as 4-aminobutyronitrile, 5-amino-rvaleronitrile, 6-aminocapronitrile and 7-aminoenantho-nitrile, very particularly preferably 6-aminocapro-nitrile.

The reductive cyclization can be carried out over a moving catalyst bed or over a stationary catalyst bed. The reaction is preferably carried out over a stationary catalyst bed (fixed bed). The fixed bed may, for example, take the form of a single dumped bed or be subdivided into a plurality of trays. The fixed bed may also be disposed in one or more reaction spaces, for example in a tube bundle reactor. The molar ratio of water to aminonitrile is generally within the range from 1 to 50, preferably within the range from 1 to 15. The reaction temperature is generally within the range from 200° to 550° C., preferably within the range from 300° to 400° C. Temperatures below 200° C. slow the vaporization of the aminonitrile and make it difficult to achieve high conversions. Temperatures above 550° C. give rise to increased formation of by-products and decomposition products.

The reaction is generally carried out at a pressure from 0.01 to 10 bar, preferably at atmospheric pressure.

The reaction may be carried out in the presence of an inert gas, for example argon or nitrogen, in which case the inert gas may be present in an excess of up to 100-fold based on the aminonitrile.

The reactor effluent, as well as the lactam product, generally comprises unconverted aminonitrile and water and also ammonia or amines and minor amounts of byproducts such as aminocarboxamides. The lactam may be recovered from the reaction effluent by customary separation processes such as distillation, extraction or crystallization.

Catalyst space velocity is typically within the range from 50 to 2000 g, preferably within the range from 500 to 2000 g, of aminonitrile per liter of catalyst per hour. Conversions based on aminonitrile are within the range from 70 to 99.9%. The selectivity of lactam formation is generally above 85%, preferably above 90%, particularly preferably above 93%, based on amino nitrile used. Selectivities above 95% are possible. These selectivity values are achieved even after catalyst on-stream times of several 100 hours.

The Examples which follow illustrate the invention.

Catalyst Preparation

Catalyst 1

Finely triturated powders of $(NH_4)H_2PO_4$ and $La(NO_3)_3 \cdot 6H_2O$ are intimately mixed with each other as precursors in a molar ratio of 3:1 in a porcelain crucible. To decompose the precursors, the mixture is maintained at 150° C. for 24 h and then at 180° C. for 12 h and subsequently slowly heated to 600° C. After four days, the material is cooled down to obtain a solid melt of $LaP_3O_9$, which is readily comminutable and processible into spall from 0.1 to 0.5 mm in particle size.

Catalyst 2

Solutions are prepared of 0.5 mol of La(NO$_3$)$_3$·6H$_2$O in 500 ml of water and of 1.5 mol of pyrophosphoric acid in 500 ml of water. The first solution is added dropwise to the second solution with stirring. Thereafter 3 mol of an aqueous concentrated NH$_3$ solution diluted with water in the ratio of 1:1 are then added dropwise while cooling with ice, and a precipitate is formed. This precipitate is separated off, washed with cold NH$_3$ solution and then dried at 150° C. for 18 h. The material thus obtained is comminuted and processed into spall from 0.1 to 0.5 mm in particle size. Thereafter the material is decomposed to the metaphosphate at 380° C. for 9.5 h and then at 550° C. for 2 h.

Catalyst 3

A solution is prepared of 0.8 mol of La(NO$_3$)$_3$·6H$_2$O in 736 ml of water and a solution of 0.92 mol of pyrophosphoric acid in 800 ml of water. The pyrophosphoric acid is adjusted to pH 10 with concentrated NH$_3$ solution, and then the metal salt solution is slowly added dropwise. The resulting precipitate is stirred at 80° C. for 1.5 h. The precipitate is centrifuged off, slurried up twice with ammoniacal water of pH 10.0 and again centrifuged off. The material thus obtained is dried at 110° C. for 12 h and thereafter processed into spall from 0.1 to 0.5 mm in particle size. The material is then calcined at 700° C. for 4 h to give a mixture of meta- and orthophosphate.

Catalyst C (Comparative Example)

The directions of EP-A 0 659 741 are followed to prepare a catalyst consisting of pure lanthanum orthophosphate. To this end, a solution of 1.0 mol of La(NO$_3$)$_3$·6H$_2$O in 3000 ml of water and a solution of 2.0 mol of (NH$_4$)$_2$HPO$_4$ in 1500 ml of water are prepared. The second solution is slowly added dropwise to the first at room temperature with stirring, and a precipitate is formed. Thereafter the pH of the suspension is adjusted to 6.0 with aqueous NH$_3$ solution. After stirring for 30 minutes, the precipitate is washed with 24 l of water on a suction filter and thereafter dried at 120° C. for 12 h. The material obtained is efficiently comminutable and processed into spall from 0.1 to 0.5 mm in particle size. The spall is finally calcined at 500° C. for 4 h. According to its XRD spectrum, the calcination product consists of pure lanthanum orthophosphate.

Cyclization Experiment

The above-described catalysts are tested in an electrically heated tubular reactor 30 mm in internal diameter, packed (starting at the bottom) with 20 ml of quartz spall, then 20 ml of catalyst as spall <0.1 mm and then 50 ml of quartz spall as vaporizer zone. After packing with catalyst, the reactor is in accordance with EP-A 0 659 741 heated to 400° C. in an air stream and then cooled down under nitrogen to the reaction temperature.

The reactor is operated in downflow mode. 6-Aminocapronitrile is charged as 50% strength by weight aqueous solution at 750 g per 1 of catalyst per hour. The reaction takes place at 360° C. at atmospheric pressure with the addition of 10 l/h of nitrogen as carrier gas. The conversion of 6-aminocapronitrile (ACN) and the selectivity for caprolactam (CPL) are determined by means of gas chromatography using an internal standard and via the mass balance. Samples are accumulated over several hours for exact quantitative measurement of selectivity and conversion. The results are summarized in Table 1.

TABLE 1

| Catalyst | CPL selectivity | ACN conversion | Time of measurement |
|---|---|---|---|
| 1 | 93.5% | 99.2% | 53 h |
|   | 91.7% | 99.2% | 124 h |
| 2 | 92.4% | 99.3% | 165 h |
|   | 92.9% | 99.3% | 555 h |
| 3 | 98.4% | 99.6% | 276 h |
|   | 97.0% | 99.6% | 494 h |
| C | 85.8% | 99.7% | 70 h |
|   | 88.5% | 99.3% | 166 h |

The measurements were carried out after the reaction had proceeded under stable conditions for at least two days. The analysis of catalyst C after 166 h revealed that it was still pure lanthanum orthophosphate.

The Examples show that the oligophosphate-containing catalysts 1 to 3 used according to the invention give higher conversions and caprolactam selectivities than a pure lanthanum orthophosphate (catalyst C).

We claim:

1. A process for preparing caprolactam which comprises: hydrolytically cyclizing 6-aminocapronitrile in the gas phase in the presence of a metal phosphite catalyst in which the catalyst is one or more oligophosphates of the formula (I)

$$(M(PO_a)_b \tag{I}$$

where M is La, a is from 2.6 to 3.5 and b is such that electrical neutrality is ensured, or a mixture of one or more oligophosphates of the formula (I) with one or more further salts of a metal of group 3 or 4 of the periodic table, including the lanthanides, with an inorganic acid.

2. The process of claim 1, wherein said further salts are selected from the group consisting of orthophosphate, sulfate, carbonate, silicate, arsenite, arsenate, antimonite, antimonate and nitrate.

3. The process of claim 1, wherein said oligophosphate is trimetaphosphate.

4. The process of claim 1, wherein the molar ratio of said further salts to said oligophosphates of the formula (I) is within the range from 1 to 5.

5. The process of claim 1, wherein said further salt is orthophosphate.

6. A process for preparing a catalyst as described in claim 1, which comprises the steps of:
   a) preparing a solution comprising a salt of said metal M;
   b) precipitating said metal M from this solution as dihydropyrophosphate and removing the precipitate comprising the metal dihydropyro-phosphate;
   c) optionally washing and drying said precipitate;
   d) calcining said precipitate.

7. A process for preparing a catalyst as described in claim 1, which comprises the steps of:
   a) preparing a mixture of ammonium dihydrogenphosphate and the nitrate of said metal M in the desired molar ratio;
   b) heating this mixture in stages to decompose the precursors and form the metal oligophosphate in a solid state reaction.

* * * * *